(12) United States Patent
Grip et al.

(10) Patent No.: US 11,100,305 B2
(45) Date of Patent: Aug. 24, 2021

(54) DISPLAY ARRANGEMENT COMPRISING ULTRASONIC BIOMETRIC SENSING SYSTEM AND METHOD FOR MANUFACTURING THE DISPLAY ARRANGEMENT

(71) Applicant: Fingerprint Cards AB, Gothenburg (SE)

(72) Inventors: Martin Grip, Höllviken (SE); Farzan Ghavanini, Gothenburg (SE)

(73) Assignee: Fingerprint Cards AB, Gothenburg (SE)

( * ) Notice: Subject to any disclaimer, the term of this patent is extended or adjusted under 35 U.S.C. 154(b) by 0 days.

(21) Appl. No.: 16/772,929

(22) PCT Filed: Dec. 11, 2018

(86) PCT No.: PCT/SE2018/051289
§ 371 (c)(1),
(2) Date: Jun. 15, 2020

(87) PCT Pub. No.: WO2019/125273
PCT Pub. Date: Jun. 27, 2019

(65) Prior Publication Data
US 2021/0165985 A1 Jun. 3, 2021

(30) Foreign Application Priority Data
Dec. 21, 2017 (SE) .................................. 1751609-7

(51) Int. Cl.
*G06K 9/00* (2006.01)
*G06K 9/22* (2006.01)
(Continued)

(52) U.S. Cl.
CPC .......... *G06K 9/0002* (2013.01); *B06B 1/0292* (2013.01); *G02F 1/13338* (2013.01);
(Continued)

(58) Field of Classification Search
USPC ......................................................... 345/173
See application file for complete search history.

(56) References Cited

U.S. PATENT DOCUMENTS

| | | | |
|---|---|---|---|
| 4,469,976 A | 9/1984 | Scott | |
| 9,984,271 B1 * | 5/2018 | King | ..................... G06F 3/0436 |
| | (Continued) | | |

FOREIGN PATENT DOCUMENTS

| | | |
|---|---|---|
| CN | 104424420 A | 3/2015 |
| CN | 106354329 A | 1/2017 |
| | (Continued) | |

OTHER PUBLICATIONS

Extended European Search Report dated Feb. 1, 2021 for European Application No. 18890547.5, 7 pages.
(Continued)

*Primary Examiner* — Chineyere D Wills-Burns
(74) *Attorney, Agent, or Firm* — RMCK Law Group, PLC

(57) ABSTRACT

There is provided a display arrangement comprising an ultrasonic biometric sensing device. The display arrangement comprises: a cover plate having a sensing surface configured to be touched by a finger; a display panel comprising a plurality of sub-layers; a plurality of ultrasonic transducers arranged along the periphery of the display arrangement and outside of an active display area of the display arrangement, each ultrasonic transducer comprising a top and bottom electrode; and ultrasonic transducer control circuitry to control the ultrasonic transducers to determine properties of an object in contact with the sensing surface. One of the sub-layers in the display panel comprises a protruding portion extending outside of an area of any other sub-layer located between the sub-layer comprising the protruding portion and the cover plate, and the plurality of
(Continued)

ultrasonic transducers are arranged on the protruding portion between the protruding portion and the cover plate.

20 Claims, 7 Drawing Sheets

(51) Int. Cl.
*B06B 1/02* (2006.01)
*G02F 1/1362* (2006.01)
*G06F 3/044* (2006.01)
*G02F 1/1333* (2006.01)
*H01L 27/32* (2006.01)
*G06F 3/041* (2006.01)

(52) U.S. Cl.
CPC ........ *G02F 1/136222* (2021.01); *G06F 3/044* (2013.01); *G06F 3/0412* (2013.01); *G06K 9/22* (2013.01); *H01L 27/322* (2013.01); *H01L 27/323* (2013.01)

(56) References Cited

U.S. PATENT DOCUMENTS

| | | | |
|---|---|---|---|
| 10,198,610 B1* | 2/2019 | Yousefpor | G06F 3/0488 |
| 2013/0234995 A1 | 9/2013 | Son et al. | |
| 2014/0003683 A1* | 1/2014 | Vieta | G06F 1/1633 |
| | | | 382/124 |
| 2014/0354596 A1 | 12/2014 | Djordjev et al. | |
| 2015/0009185 A1* | 1/2015 | Shi | G06F 3/0436 |
| | | | 345/177 |
| 2015/0036065 A1 | 2/2015 | Yousefpor et al. | |
| 2015/0063663 A1 | 3/2015 | Wu | |
| 2015/0189136 A1 | 7/2015 | Chung et al. | |
| 2016/0038974 A1 | 2/2016 | Gubbini et al. | |
| 2016/0350573 A1 | 12/2016 | Kitchens et al. | |
| 2017/0053151 A1* | 2/2017 | Yeke Yazandoost | |
| | | | A61B 5/6898 |
| 2017/0090028 A1* | 3/2017 | Djordjev | G01S 7/521 |
| 2017/0110504 A1* | 4/2017 | Panchawagh | B06B 1/0207 |
| 2017/0330012 A1 | 11/2017 | Salvia et al. | |
| 2019/0065805 A1 | 2/2019 | Zhao | |
| 2020/0265203 A1* | 8/2020 | Tuneld | G06F 3/0488 |
| 2020/0279088 A1* | 9/2020 | Lundahl | G06K 9/0002 |

FOREIGN PATENT DOCUMENTS

| | | |
|---|---|---|
| CN | 106530968 A | 3/2017 |
| CN | 106774805 A | 5/2017 |
| TW | 201508582 A | 3/2015 |
| WO | 2015009635 A1 | 1/2015 |
| WO | 2017052836 A1 | 3/2017 |

OTHER PUBLICATIONS

PCT International Search Report and Written Opinion dated Feb. 8, 2019 for International Application No. PCT/SE2018/051289, 9 pages.

* cited by examiner

DISPLAY ARRANGEMENT COMPRISING ULTRASONIC BIOMETRIC SENSING SYSTEM AND METHOD FOR MANUFACTURING THE DISPLAY ARRANGEMENT

CROSS-REFERENCE TO RELATED APPLICATIONS

This application is a 371 U.S. National Stage of International Application No. PCT/SE2018/051289, filed Dec. 11, 2018, which claims priority to Swedish Patent Application No. 1751609-7, filed Dec. 21, 2017. The disclosures of each of the above applications are incorporated herein by reference in their entirety.

FIELD OF THE INVENTION

The present invention relates to a display arrangement comprising ultrasonic transducer devices for use in an acoustic biometric imaging system and to a method for manufacturing such a display arrangement.

BACKGROUND OF THE INVENTION

Biometric systems are widely used as means for increasing the convenience and security of personal electronic devices, such as mobile phones etc. Fingerprint sensing systems, in particular, are now included in a large proportion of all newly released personal communication devices, such as mobile phones.

Due to their excellent performance and relatively low cost, capacitive fingerprint sensors are used in an overwhelming majority of all biometric systems.

Among other fingerprint sensing technologies, ultrasonic sensing also has the potential to provide advantageous performance, such as the ability to acquire fingerprint (or palm print) images from very moist fingers etc.

One class of ultrasonic fingerprint systems of particular interest are systems in which acoustic signals are transmitted along a surface of a device member to be touched by a user, and a fingerprint (palm print) representation is determined based on received acoustic signals resulting from the interaction between the transmitted acoustic signals and an interface between the device member and the user's skin.

Such ultrasonic fingerprint sensing systems, which are, for example, generally described in US 2017/0053151 may provide for controllable resolution, and allow for a larger sensing area, which may be optically transparent, without the cost of the fingerprint sensing system necessarily scaling with the sensing area.

Although the general principle of such ultrasonic fingerprint sensing is known, there appear to be remaining challenges to be overcome. For instance, it would be desirable to provide for easy and cost-efficient integration of ultrasonic transducer devices suitable for use in such ultrasonic fingerprint sensing systems.

SUMMARY

In view of above-mentioned and other drawbacks of the prior art, it is an object of the present invention to provide an improved display arrangement for biometric sensing and a method for manufacturing such a display arrangement.

According to a first aspect of the invention, there is provided a display arrangement comprising an ultrasonic biometric sensing device for in-display biometric sensing.

The display arrangement comprises: a cover plate having a sensing surface configured to be touched by a finger; a display panel comprising a plurality of sub-layers; a plurality of ultrasonic transducers arranged along the periphery of the display arrangement and outside of an active display area of the display arrangement, wherein the ultrasonic transducers are non-overlapping with an active sensing area (104) of the biometric sensing device, each ultrasonic transducer comprising an electrically conductive top electrode located on a first side of the transducer facing the cover plate and an electrically conductive bottom electrode on a second side of the transducer, the second side opposing the first side; and ultrasonic transducer control circuitry connected to each of the ultrasonic transducers and configured to control the ultrasonic transducers to emit an ultrasonic signal propagating in the cover plate, to receive an ultrasonic signal having been influenced by an object in contact with the sensing surface and to determine properties of the object based on the received ultrasonic signal; wherein one of the sub-layers in the display panel comprises a protruding portion extending outside of an area of any other sub-layer located between the sub-layer comprising the protruding portion and the cover plate, and wherein the plurality of ultrasonic transducers are arranged on the protruding portion between the protruding portion and the cover plate such that a direct mechanical coupling between the transducer and the cover plate is formed.

A display panel is in the present context interpreted to mean a display comprising all the layers and components required in presently known display technologies. The display may also comprise an in-cell or on-cell touch screen technology.

The ultrasonic transducers typically comprise a piezoelectric material generating an ultrasonic signal in response to an electric field applied across the material by means of the top and bottom electrodes. In principle, it is also possible to use other types of ultrasonic transducers, such as capacitive micromachined ultrasonic transducers (CMUT).

The ultrasonic transducers will be described herein as transceivers being capable of both transmitting and receiving ultrasonic signals. However, it is also possible to form a system comprising individual and separate ultrasonic transmitters and receivers.

The ultrasonic transducer control circuitry is configured to control the transmission and reception of ultrasonic signals and is considered to comprise appropriate signal processing circuitry required for extracting an image from the received ultrasonic signals. It is typically desirable to capture an image of the finger in contact with the sensing surface, which preferably is the entire surface of the cover plate being encircled by the ultrasonic transducers to thereby determine a fingerprint for biometric identification and verification.

A display panel is considered to comprise at least two sub-layers, and the number and nature of layers vary depending on the display technology used or the specific display manufacturer. The key to the arrangement of ultrasonic transducers described herein is that at least one sub layer is configured to extend outside of the active display area. In practice, all of the layers may extend outside of an effective display area. Moreover, none of the sub-layers located between the protruding sub-layer and the cover plate should preferably protrude to cover or block the sub-layer comprising the ultrasonic transducers, at least not at the locations of the ultrasonic transducers. For the ultrasonic transducers to efficiently inject an ultrasonic signal into the cover plate, a direct mechanical coupling between the transducer and the cover plate is required. Accordingly, no part of the display panel should be located between the transducer and the cover plate.

The present invention is based on the realization that an in-display biometric sensing arrangement can be achieved by arranging ultrasonic transducers at the periphery of a display panel. In particular, by arranging the ultrasonic transducers on an already existing structure in the display panel, the described biometric sensing arrangement can be integrated in a display panel with a minimum of modifications of an existing display manufacturing process. Moreover, the described biometric sensing system would not influence the display properties since the components of the sensing system are located outside of an active display area.

According to one embodiment of the invention, the display panel may comprise a TFT-layer (thin film transistor) and a TFT-substrate layer on which the TFT-layer is formed, and wherein the protruding portion is formed in the TFT-substrate layer. The TFT-substrate layer may be a glass or plastic layer used to form TFT-devices on for controlling the display pixels. Accordingly, the TFT-layer can be assumed to have mechanical properties suitable for arrangement of the ultrasonic transducers.

According to one embodiment of the invention, the display panel may comprise a color filter layer, and wherein the protruding portion is formed in the color filter layer. In an LCD-type display panel, the color filter is arranged on a glass substrate, and the protruding portion would thus be formed by the glass substrate and the color filter, where the transducers would be arranged on top of the color filter substrate. A potential advantage of arranging the transducers on the color filter layer would be that the transducers will be arranged closer to the cover glass of the display panel.

According to one embodiment of the invention, the display panel may comprise an OLED-layer (organic light emitting diode) and an OLED-substrate layer on which the OLED-layer is formed, wherein the protruding portion is formed in the OLED-substrate layer. The OLED-layer can be considered to comprise the plurality of layers required for forming an OLED-display.

According to one embodiment of the invention, the display panel may comprise an LCD-layer (liquid crystal display) and an LCD-substrate layer on which the LCD-layer is formed, wherein the protruding portion is formed in the LCD-substrate layer. The LCD-layer can be considered to comprise the plurality of layers required for forming an LCD-display.

Both an OLED and an LCD display may comprise TFT technology to control the display pixels, and the both an OLED-substrate and the LCD-substrate may thus be seen as a TFT-substrate. However, there may also be other layers in the respective display panels which are suitable for placing the transducers. It is also possible to provide a dedicated support layer comprising the protruding portion. Such a support layer may then be arranged either above or below the active layers of the display panel.

According to one embodiment of the invention, the display panel may further comprise a capacitive touch sensitive panel, wherein the protruding portion is formed in a substrate layer of the touch sensitive panel. The touch sensitive panel may for example be a capacitive panel, located above the active display layers, comprising at least one transparent substrate layer carrying the components of the touch sensitive panel. In an LCD-display, a touch sensitive layer may be formed on top of the color filter layer.

According to one embodiment of the invention at least one of the electrically conductive top electrode and the electrically conductive bottom electrode may advantageously be routed and connected to the ultrasonic transducer control circuitry on the layer comprising the protruding portion. Thereby, the ultrasonic transducers can be placed with the bottom electrode facing the surface of the protruding portion such that the transducer is directly connected to conductive lines present ion the protruding portion. This has the advantage that the conductive lines can be manufactured separately on the layer comprising the protruding portion and that no additional connections are required after placing the transducers in contact with the conductive lines. In order to connect both of the first and second electrode to a conductive line located on the protruding portion, the top electrode is routed down to the bottom of the transducer. Such a transducer may be achieved by forming a specific package where the bottom of the package comprises connection for both the top and the bottom electrodes. The routing from the top to the bottom of the transducer is preferable formed on the side of the transducer.

In one embodiment of the invention, where the protruding portion is formed in a TFT-substrate layer, at least one of the electrically conductive top electrode and the electrically conductive bottom electrode may be routed and connected to the ultrasonic transducer control circuitry in the same conductive layer on the same substrate on which the TFT-layer is formed. A TFT layer comprises at least one electrically conductive layer, and by forming the electrically conductive lines connecting the transducers to the transducer control circuitry in one of the conductive layers of the TFT-layer, an already existing and well established manufacturing process can be used with only minor modifications. A TFT-manufacturing process typically has a high accuracy and resolution, enabling the fabrication of small features. This enables the formation of small conductive lines to thereby minimize the area coverage of the conductive lines. Typically, the TFT-manufacturing process can produce features having a size in the range of a few micrometers. However, the conductive lines connecting the transducers may have to be larger than the minimum achievable features size due to the resistance of small conductive lines.

According to one embodiment of the invention, where the protruding portion is formed in a touch panel layer, at least one of the electrically conductive top electrode and the electrically conductive bottom electrode may be routed and connected to the ultrasonic transducer control circuitry in a conductive layer comprised in the touch sensitive panel. In a similar manner as described above for the TFT-layer, also the touch sensitive layer can be assumed to comprise conductive layers, making it possible to use an existing manufacturing process to form the electrically conductive lines for connecting the transducers to corresponding control circuitry.

According to one embodiment of the invention, the ultrasonic transducer control circuitry may be integrated in display control circuitry of the display arrangement. This means that the display control circuitry comprises functionality for controlling the ultrasonic transducers to emit an ultrasonic signal and for acquiring an image from the received signals. Thereby, there is to need to make room for and arrange dedicated control circuitry for the ultrasonic transducers. Moreover, if the electrodes of the transducers are connected to conductive lines in a conductive layer already existing in the display, the connection of the transducers to the control circuitry is simplified. In a similar manner, the ultrasonic transducer control circuitry may be integrated in touch panel control circuitry of the display arrangement.

According to one embodiment of the invention, the display arrangement may further comprise an ultrasonic transducer comprising one electrically conductive top electrode and a plurality of electrically conductive bottom electrodes such that an active portion of the transducer is defined by the plurality of electrically conductive bottom electrodes. An active portion of the transducer is thus defined as the portion of the transducer located between one bottom electrode and the top electrode. Thereby, the number of required connections to the transducer can be reduced since only one top electrode need to be used in a transducer structure effectively comprising a number of transducers. In a similar manner, the ultrasonic transducer may comprise one electrically conductive bottom electrode and a plurality of electrically conductive top electrodes. Furthermore, it is also possible to provide an ultrasonic transducer comprising a plurality of electrodes on each of the top side and the bottom side. The specific electrode configuration can thus be selected based on what is most convenient for a given application.

According to one embodiment of the invention, at least one of the electrically conductive top electrode and the electrically conductive bottom electrode may be routed and connected to the ultrasonic transducer control circuitry via the cover plate. In some applications, it may be convenient to connect only the top electrode to conductive lines on the cover plate, where routing to control circuitry is likewise located on the cover plate. It is also possible to electrically connect both bottom and top electrodes to control circuitry via conductive lines the cover plate. The bottom electrode is then routed to the top side of the transducer and connected to the control circuitry via the conductive lines on the cover plate.

According to one embodiment of the invention may further comprise a connection material located between the transducer and the cover plate, mechanically coupling the transducer to the cover plate. It is important to form a rigid mechanical coupling between the transducer and the cover plate in order to avoid dampening or other losses when the ultrasonic signal is transmitted from the transducer into the cover plate. The connection material may be a solder material, and adhesive or the like. If the cover plate comprises conductive lines for connecting the transducers to the transducer control circuitry, the filling material is electrically conductive to form an electrical connection between the top electrodes of the transducers and the conductive lines on the cover plate. It is also possible to connect the cover plate to the transducer by means of direct bonding or other bonding technologies.

According to one embodiment of the invention, the electrically conductive bottom electrode may advantageously comprise an electrically conductive spacer arranged between the bottom electrode and the protruding portion. The distance between the protruding portion and the cover plate may vary depending on in which layer the protruding portion is formed and on the specific display design. Accordingly, the described spacer provides an easy way to adapt the described transducer to fit between a protruding portion of a sub-layer in the display and the cover plate irrespective of the distance between protruding portion and the cover plate. The spacer is located between the bottom electrode and the protruding portion since it is preferable to minimize the distance between the transducer and the cover plate, thereby making it less preferable to arrange a spacer between the top electrode and the cover plate.

According to a second aspect of the invention, there is provided a method for manufacturing a display arrangement. The method comprises providing a display panel comprising a plurality of sub-layers, wherein one of the sub-layers in the display panel comprises a protruding portion extending outside of an area of any other sub-layer; forming electrically conductive lines on the protruding portion, wherein the electrically conductive lines are configured to connect each ultrasonic transducer to ultrasonic transducer control circuitry configured to control the ultrasonic transducers to emit an ultrasonic signal propagating in a cover plate, to receive an ultrasonic signal having been influenced by an object in contact with a sensing surface of the cover plate and to determine properties of the object based on the received ultrasonic signal; and arranging a plurality of ultrasonic transducers on the protruding portion along the periphery of the display arrangement and outside of an active display area of the display arrangement, each ultrasonic transducer comprising an electrically conductive top electrode located on a first side of the transducer and an electrically conductive bottom electrode on a second side of the transducer, the second side opposing the first side, wherein each electrically conductive bottom electrode is connected to a corresponding electrically conductive line on the protruding portion; arranging a cover plate on the display panel such that the ultrasonic transducers are located between the cover plate and the protruding portion, the cover plate having a sensing surface configured to be touched by a finger.

Effects and features of the second aspect of the invention are largely analogous to those described above in connection with the first aspect of the invention.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein.

DETAILED DESCRIPTION OF EXAMPLE EMBODIMENTS

In the present detailed description, various embodiments of the display arrangement for biometric sensing and method for manufacturing the display arrangement according to the present invention are mainly described with reference to a display arrangement in a smartphone, wherein an ultrasonic transducer array of the display arrangement enables sensing of a fingerprint of a finger placed on an exterior surface of the display.

Figure 1A:
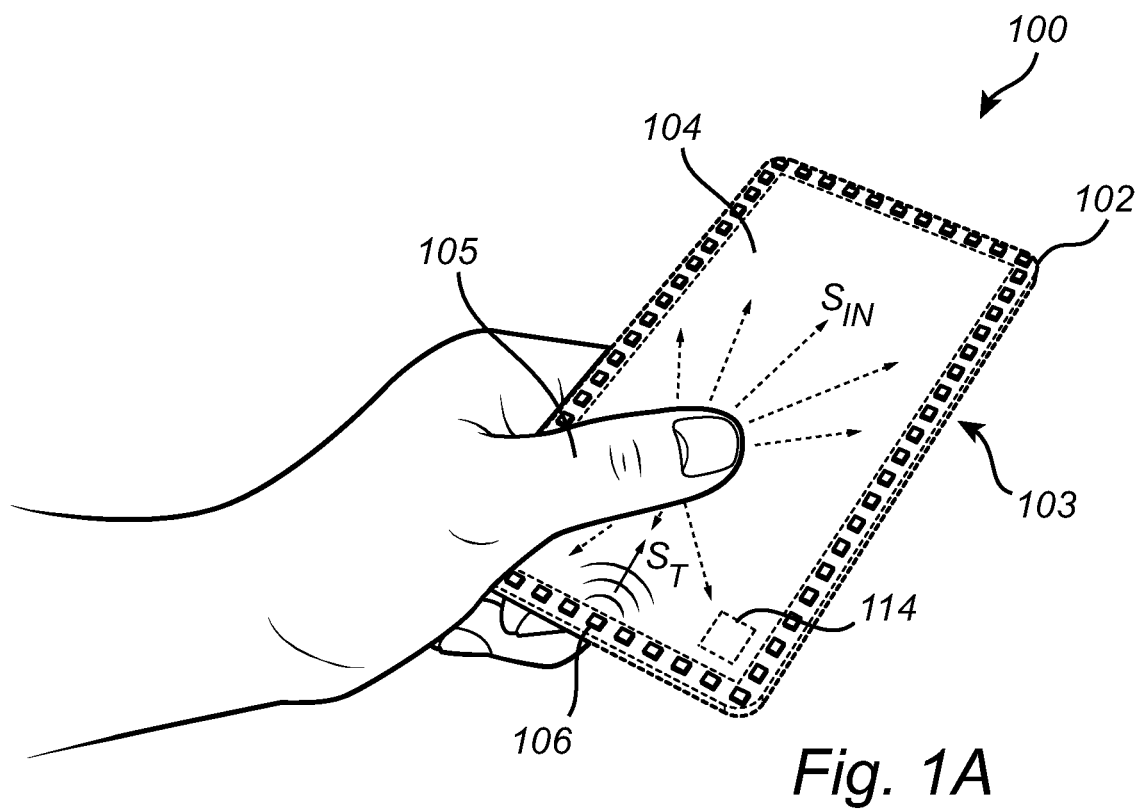
FIG. 1A schematically illustrates a display arrangement according to an embodiment of the invention.

FIG. 1A schematically illustrates an electronic device in the form of a smartphone 100 comprising a display panel 102 included in a display arrangement according to an embodiment of the invention. The display arrangement comprises a cover structure in the form of a cover glass 103, having an exterior surface 104 configured to be touched by a finger 105. The cover plate 103 is here illustrated as a transparent cover glass of a type commonly used in a display panel 102 of the smartphone 100. However, the cover plate 103 may equally well be a non-transparent cover plate as long as its acoustic properties allows for propagation of ultrasound energy.

The display arrangement further comprises a plurality of ultrasonic transducers 106 connected to the cover plate 103 and located at the periphery of the cover plate 102. Accordingly, the ultrasonic transducers 106 are here illustrated as being non-overlapping with an active sensing area 104 of the biometric sensing device formed by the ultrasonic transducers 106 and the cover plate 103. However, the ultrasonic transducers 106 may also be arranged and configured such that they overlap an active sensing area. FIG. 1A illustrates an example distribution of the transducers 106 where the transducers 106 are evenly distributed around the periphery of the cover plate 103 along all sides of the display panel 102. However, other transducer distributions are equally possible, such as arranging the transducers 106 on three sides of the display panel 102, and also irregular distributions are possible.

Figure 1B:
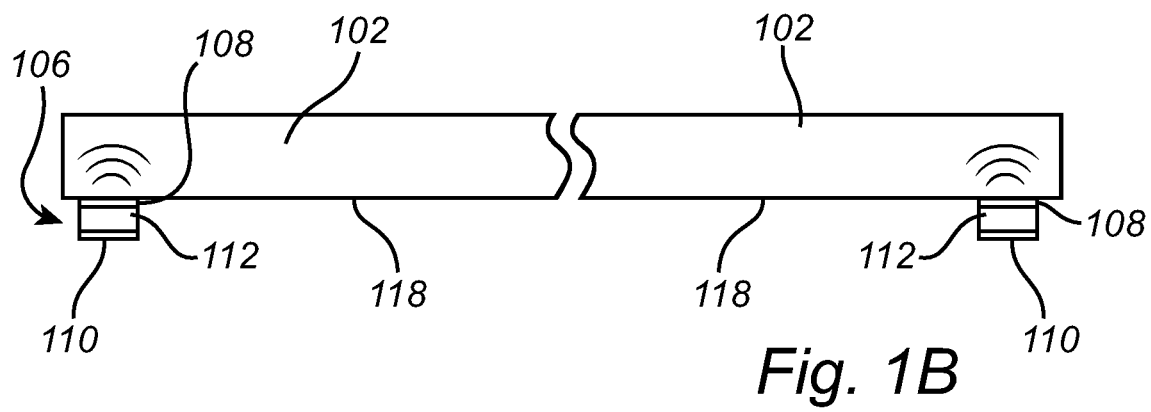
FIG. 1B is a cross section view of a display arrangement according to an embodiment of the invention.

FIG. 1B is a cross section view of the cover plate 103 where it is illustrated that the ultrasonic transducers 106 are arranged underneath the cover plate 103 and attached to the bottom surface 118 of the cover plate 103. The ultrasonic transducer 106 is a piezoelectric transducer comprising a first electrode 108 and second electrode 110 arranged on opposing sides of a piezoelectric element 112 such that by controlling the voltage of the two electrodes 108, 110, an ultrasonic signal can be generated which propagates into the cover plate 103. An ultrasonic transducer 106 can have different configurations depending on the type of transducer and also depending on the specific transducer package used. Accordingly the size and shape of the transducer as well as electrode configurations may vary. It is also possible to use other types of devices for the generation of ultrasonic signals such as micromachined ultrasonic transducers (MUTs), including both capacitive (cMUTs) and piezoelectric types (pMUTs). Moreover, additional control circuitry is required for controlling the transducer to emit an acoustic signal having the required properties with respect to e.g. amplitude, pulse shape and timing. However, such control circuitry for ultrasonic transducers is well known to the skilled person and will not be discussed in detail herein.

Each ultrasonic transducer 106 is configured to transmit an acoustic signal $S_T$ propagating in the plane of the cover plate 103 and to receive an ultrasonic signal $S_{IN}$ having been influenced by an object 105, here represented by a finger 105, in contact with the sensing surface 104.

The acoustic interaction signals $S_{IN}$ are presently believed to mainly be due to so-called contact scattering at the contact area between the cover plate 103 and the skin of the user (finger 105). The acoustic interaction at the point of contact between the finger 105 and the cover plate 103 may also give rise to refraction, diffraction, dispersion and dissipation of the acoustic transmit signal $S_T$. Accordingly, the interaction signals $S_{IN}$ are advantageously analyzed based on the described interaction phenomena to determine properties of the finger 105 based on the received ultrasonic signal.

The acoustic transmit signal $S_T$ may advantageously be provided in the form of a pulse train of short pulses, and the acoustic interaction signals $S_{IN}$, which may be measured by different receiving ultrasonic transducers 106, are impulse responses. The impulse response data carried by the acoustic interaction signals $S_{IN}$ can in turn be used to reconstruct a representation of the contact area (the fingerprint) using a reconstruction procedure similar to methods used in ultrasound reflection tomography.

It should be understood that the "representation" of the fingerprint of the user may be any information extracted based on the received acoustic interaction signals $S_{IN}$, which is useful for assessing the similarity between fingerprint representations acquired at different times. For instance, the representation may comprise descriptions of fingerprint features (such as so-called minutiae) and information about the positional relationship between the fingerprint features. Alternatively, the representation may be a fingerprint image, or a compressed version of the image. For example, the image may be binarized and/or skeletonized. Moreover, the fingerprint representation may be the above-mentioned impulse response representation.

Accordingly, the ultrasonic transducers 106 and associated control circuitry are configured to determine properties of the object based on the received ultrasonic signal $S_{IN}$. The plurality of ultrasonic transducers 106 are connected to and controlled by ultrasonic transducer control circuitry 114. The control circuitry 114 for controlling the transducers 106 may be embodied in many different ways. The control circuitry 114 may for example be one central control unit 114 responsible for determining the properties of the acoustic signals $S_T$ to be transmitted, and for analyzing the subsequent interaction signals $S_{IN}$. Moreover, each transducer 106 may additionally comprise control circuitry for performing specified actions based on a received command.

The control unit 114 may include a microprocessor, microcontroller, programmable digital signal processor or another programmable device. The control unit 114 may also, or instead, include an application specific integrated circuit, a programmable gate array or programmable array logic, a programmable logic device, or a digital signal processor. Where the control unit 114 includes a programmable device such as the microprocessor, microcontroller or programmable digital signal processor mentioned above, the processor may further include computer executable code that controls operation of the programmable device.

The functionality of the control circuitry 114 may also be integrated in control circuitry used for controlling the display panel 102 or other features of the smartphone 100.

Figure 2:
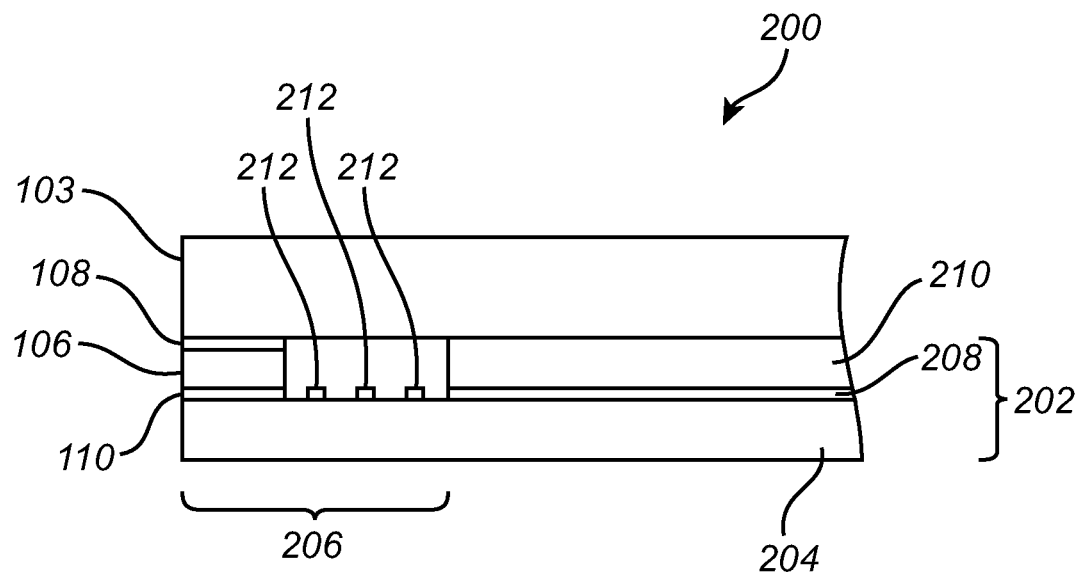
FIG. 2 schematically illustrates a display arrangement according to an embodiment of the invention.

FIG. 2 is a cross section view of a display arrangement 200 according to an embodiment of the invention. The biometric sensing functionality is thus provided by the plurality of ultrasonic transducers 106, the cover plate 103 and associated control circuitry 114 as described above.

The display arrangement 200 of FIG. 2 comprises a cover plate 103 and a display panel 102 comprising a plurality of sub-layers 202. It can further be seen that a plurality of ultrasonic transducers 106 as described above with reference to FIG. 1B. The ultrasonic transducer 106 is arranged at the edge of the display arrangement 200 underneath the cover plate 103. The display arrangement 200 may further comprise a frame (not shown) around the display panel 102.

Of the sub-layers 202 in the display panel 102, one of the sub-layers 204 in the display panel comprises a protruding portion 206 extending outside of an area of any other sub-layer 206, 208 located between the sub-layer 204 comprising the protruding portion 206 and the cover plate 103, The ultrasonic transducer 106 is arranged on the protruding portion 206 between the protruding portion 206 and the cover plate 103. Thereby, the ultrasonic transducer 106 may be arranged directly in contact with the cover plate 103 to provide the best possible coupling pf generated acoustic signals from the transducer into the cover plate 103.

According to one embodiment, the display panel 102 comprises a TFT-layer 208 and a TFT-substrate layer 204 on which the TFT-layer 208 is formed, and wherein the protruding portion 206 is formed in the TFT-substrate layer 204.

When using the TFT-substrate 204 to form the protruding portion 206, a further advantage is provided since the electrically conductive TFT-layer can be used also to form electrical connections 212 between the transducer 106 and associated control circuitry, thereby utilizing an already existing process step.

If the display panel is an OLED panel, the TFT-substrate layer 204 may be a glass or plastic layer, and if the display panel is an LCD panel, the TFT-substrate layer is typically a glass layer. Moreover, FIG. 2 illustrates an intermediate layer 210 between the TFT-layer 208 and the cover plate 103. If the display panel is an LCD panel, the intermediate layer 210 may be a color filter layer. An OLED display panel on the other hand does not necessarily comprise a color filter layer. For an OLED panel, the intermediate layer 210 may be an encapsulation layer However, there are OLED-implementations comprising a color filter layer. An example is an implementation where all of the PLED pixels are white, thereby requiring a color layer. There may also be additional layers located between the TFT-layer and the intermediate layer which are not shown herein.

Figure 3:
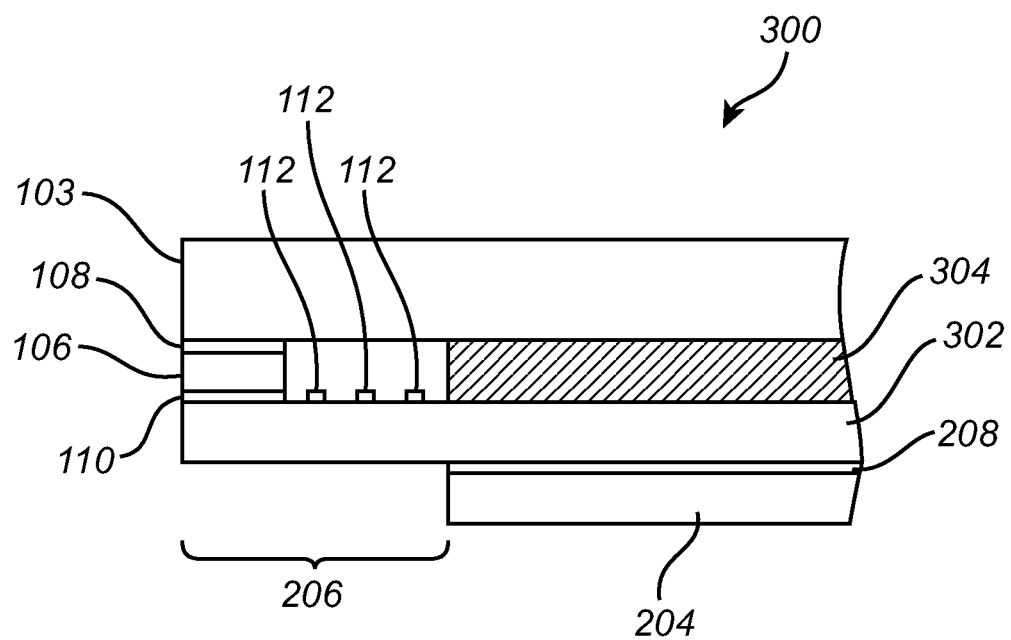
FIG. 3 schematically illustrates a display arrangement according to an embodiment of the invention.

FIG. 3 schematically illustrates an embodiment of the display arrangement where the protruding portion 206 is formed in a color filter layer 302 which is located above the TFT-layer 208 and TFT-substrate layer 210. The layer 304 located between the color filter layer 302 and the cover plate 302 may for example be a polarizing layer 304. Here, the electrical connections 212 are formed on the substrate of the color filter layer 302. The pigment layer of the color filter 302 may be arranged on the underside of the substrate.

Figure 4:
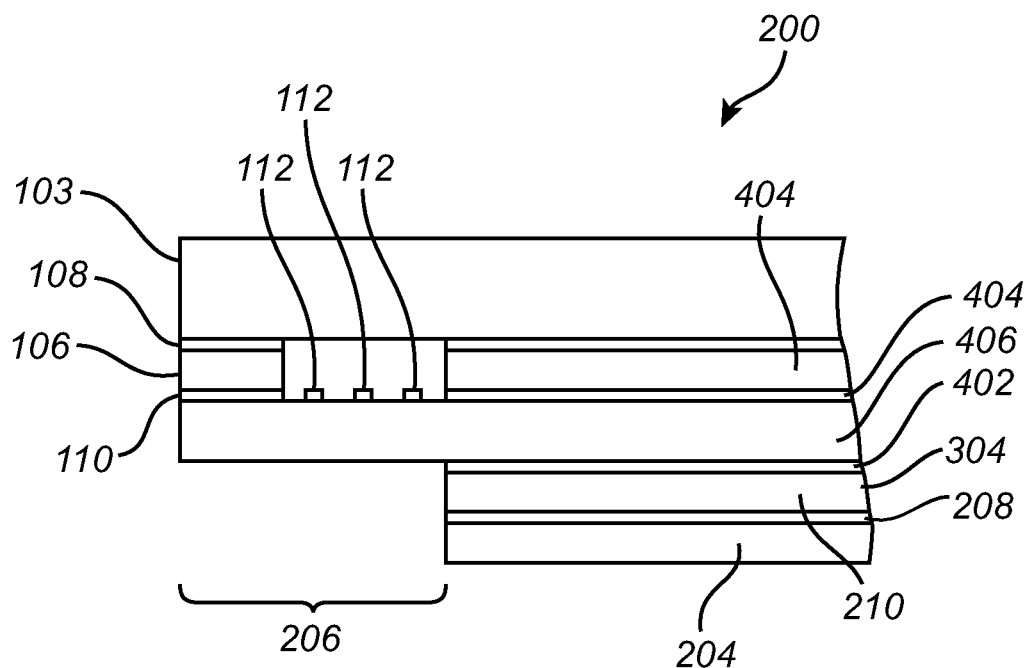
FIG. 4 schematically illustrates a display arrangement according to an embodiment of the invention.

FIG. 4 schematically illustrates an embodiment of the display arrangement where the protruding portion 206 is formed in a substrate layer 406 of a capacitive touch panel. The touch panel may for example be a projected capacitive multi-touch technology touch panel comprising two electrode layers 402, 404 (transmit, Tx, and receive, Rx) separated by a dielectric substrate layer 406. In the described embodiment, the conductive lines can be formed in the same step as the formation of the electrodes of the top electrode layer 402. In FIG. 3, the protruding portion 206 is illustrated as protruding outside of all of the remaining layers 204, 208, 304 of the display panel. However, any layer located below the layer 302 comprising the protruding portion 206 may extend as far as the layer 302 comprising the protruding portion 206, or even further if that is preferred.

In an exemplary embodiment, the transducer 106 has a thickness of approximately 50 μm, which gives an indication of the required thicknesses of the layers in the display panel for various embodiments. To provide examples, a touch panel layer 402,404 may have a thickness of approximately 50 μm, a polarizer may have a thickness of 50 μm, and a color filter 210 may have a thickness of approximately 200 μm. The thickness of other intermediate layers such as adhesive layers and electrically conductive are also taken into account when determining the preferred configuration and position of the transducers. Moreover, the thickness of both the respective layers and of the transducer 106 can be adapted to fit into a desired configuration.

Figure 5:
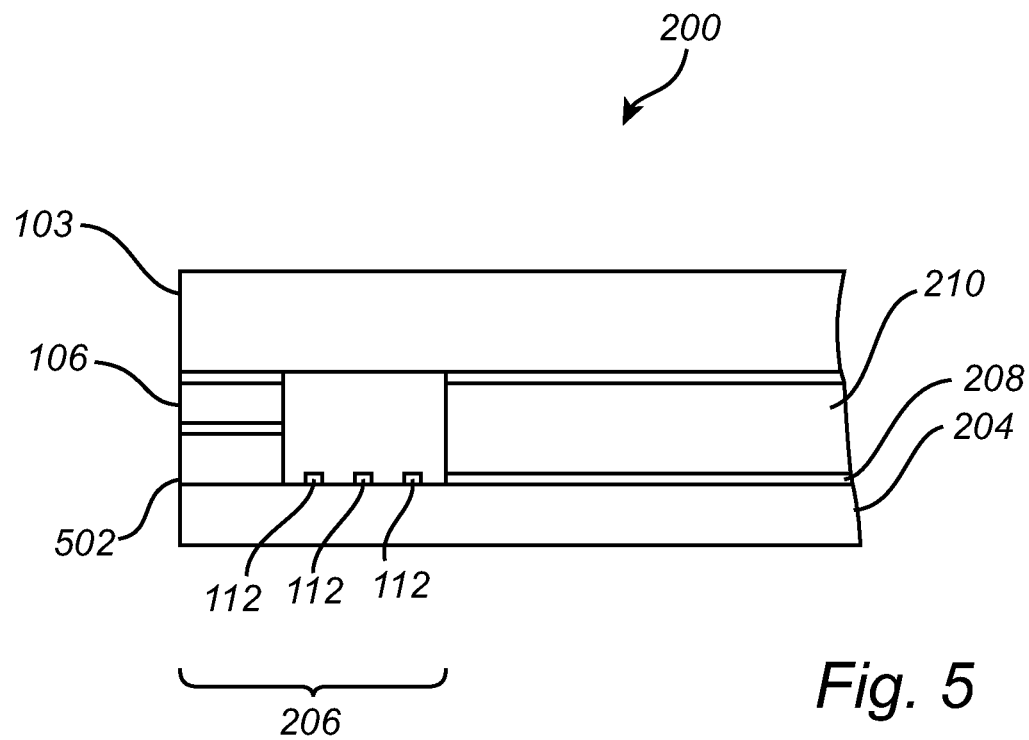
FIG. 5 schematically illustrates a display arrangement according to an embodiment of the invention.

Furthermore, if it is not possible to modify the thicknesses of the required layers, a spacer 502 of suitable thickness may be arranged between the transducer 106 and the protruding portion 206 as illustrated in FIG. 5. Thereby, it is only the thickness of the spacer element 502 which has to be adapted for the transducer to fit into any given display configuration, under the condition that the distance between the protruding portion 206 and the cover plate 103 is larger than the thickness of the transducer 106.

The spacer 502 is electrically conductive in order to form an electrical connection between the bottom electrode 110 of the transducer 106 and the surface of the layer comprising the protruding portion where the electrical conductors are located. However, it is also possible to form all of the required signal routing in electrical connectors on the underside of the cover plate 103, in which case an electrically insulating spacer may be used. Furthermore, there is preferable an adhesive layer (not shown) located between the top electrode 108 of the transducer 106 and the cover plate 103, both the mechanically attach the transducer 106 to the cover plate 103 and to ensure that there is no air gap between the transducer 106 and the cover plate 103, thereby providing a good mechanical coupling between the transducer 106 and the cover plate 103. The adhesive layer may be glue or it may be a solder material. It is also possible to directly bond the transducer 106 to the cover plate 103.

Figure 6A:
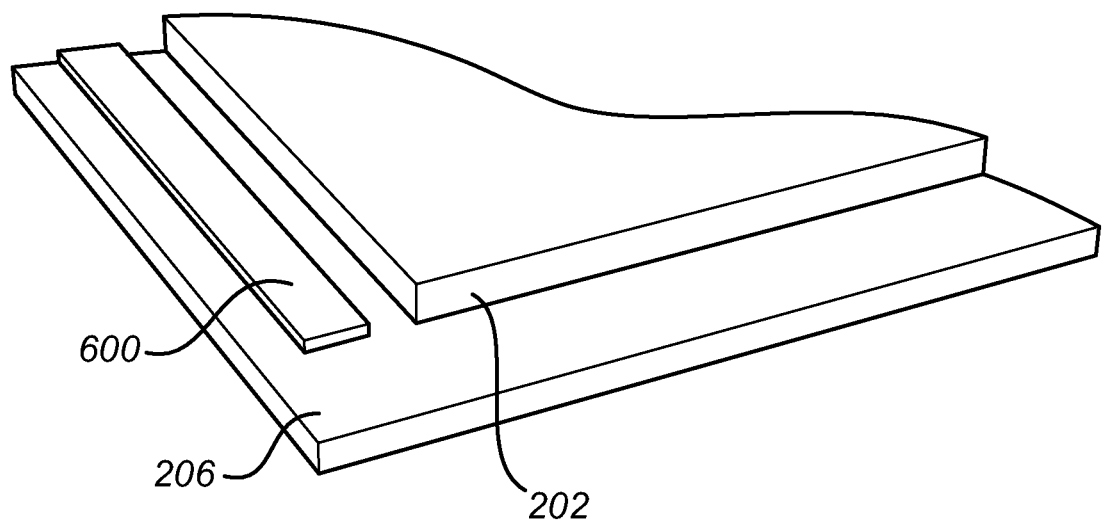
FIG. 6 schematically illustrates a transducer configuration of a display arrangement according to an embodiment of the invention.
Figure 6B:
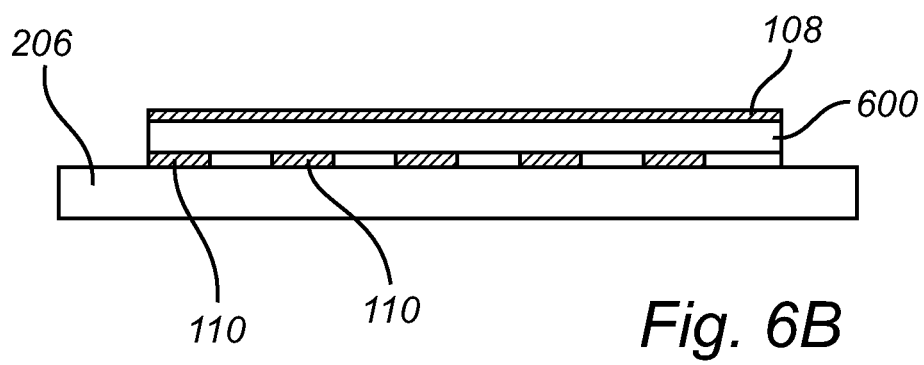

FIGS. 6A-B schematically illustrate an embodiment where the transducer 106 comprises a larger of piezoelectric transducer element 600 arranged on the protruding portion 206 of the display panel 102 illustrated in FIG. 6A. The transducer 106 has one top electrode 108 and a plurality of bottom electrodes 110 as can be seen in the side view of FIG. 6B. The active transducer area is thereby defined by the plurality of bottom electrodes 110, with a common top electrode 108 for all of the transducers 106 in the large transducer element 600. During operation, the top electrode 108 may be grounded while the bottom electrodes 110 are individually controllable to only activate the specifically addressed transducer 106.

Figure 7:
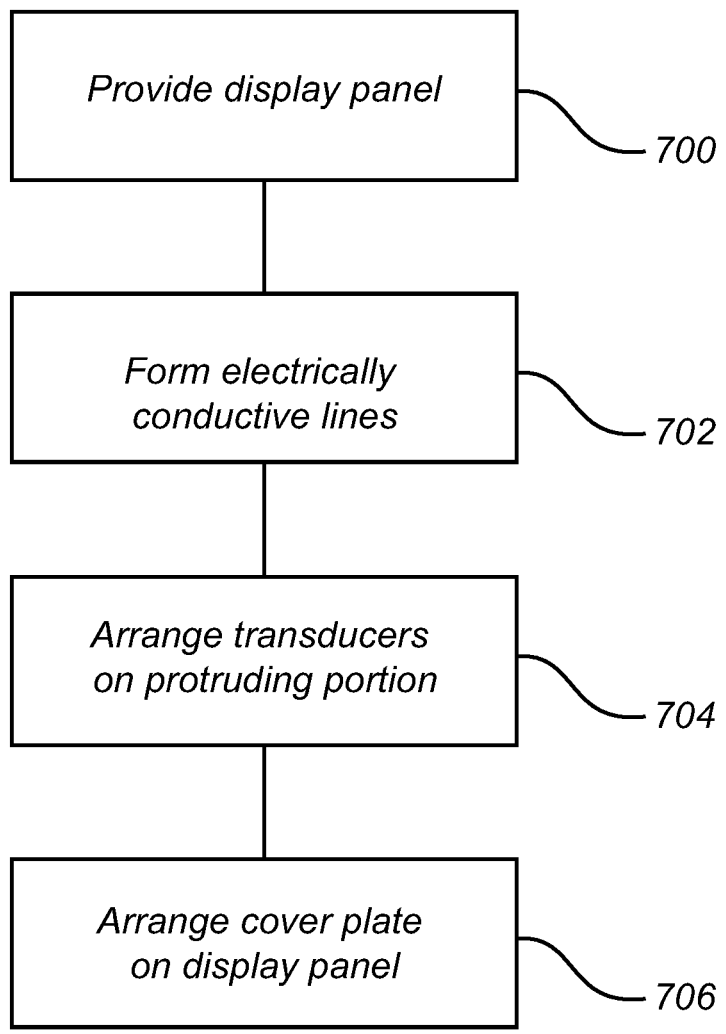
FIG. 7 is a flow chart outlining the general steps of manufacturing a display arrangement according to an embodiment of the invention.
Figure 8A:
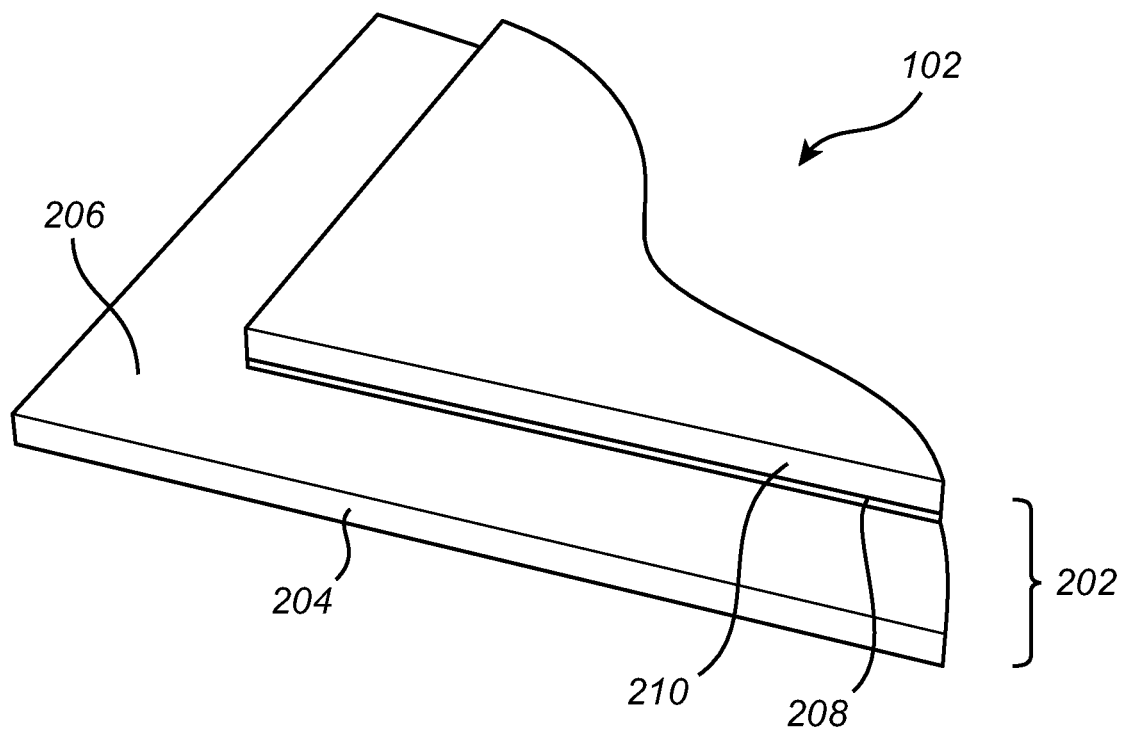
FIGS. 8A-D schematically illustrate steps of a manufacturing method according to an embodiment of the invention.
Figure 8B:
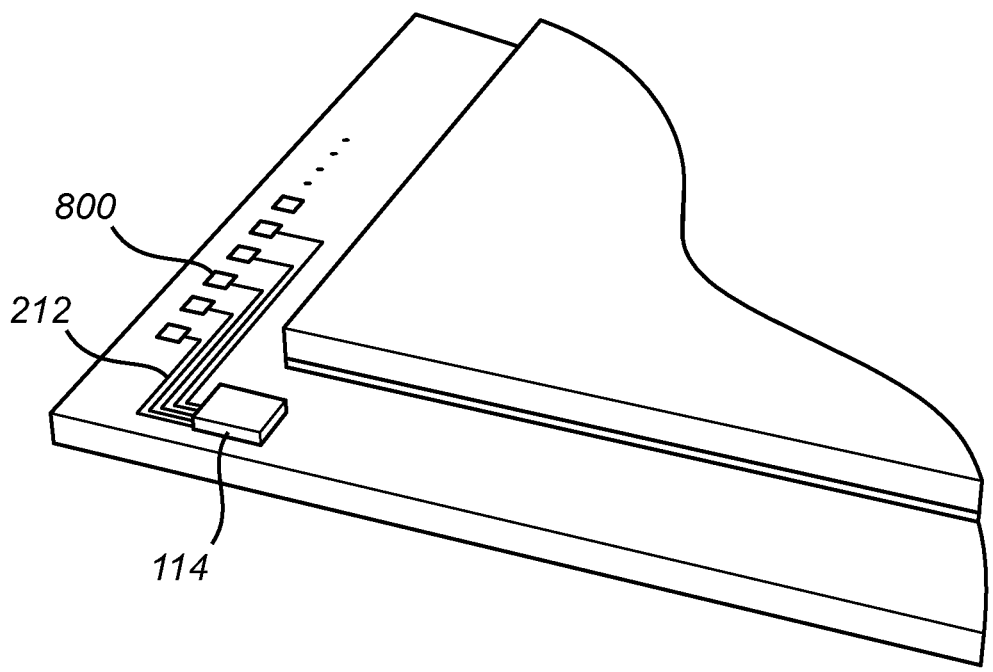
Figure 8C:
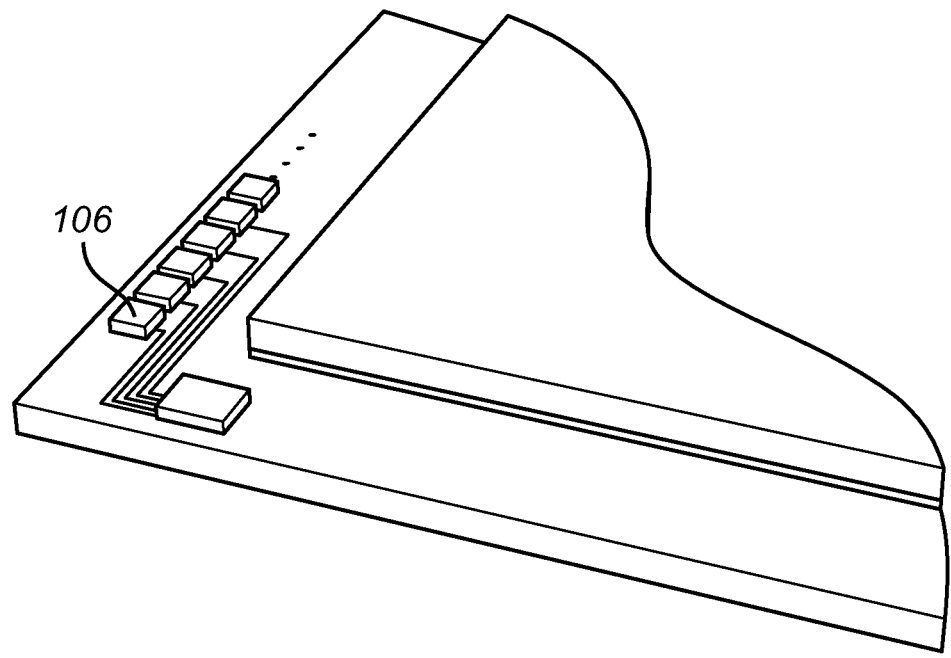
Figure 8D:
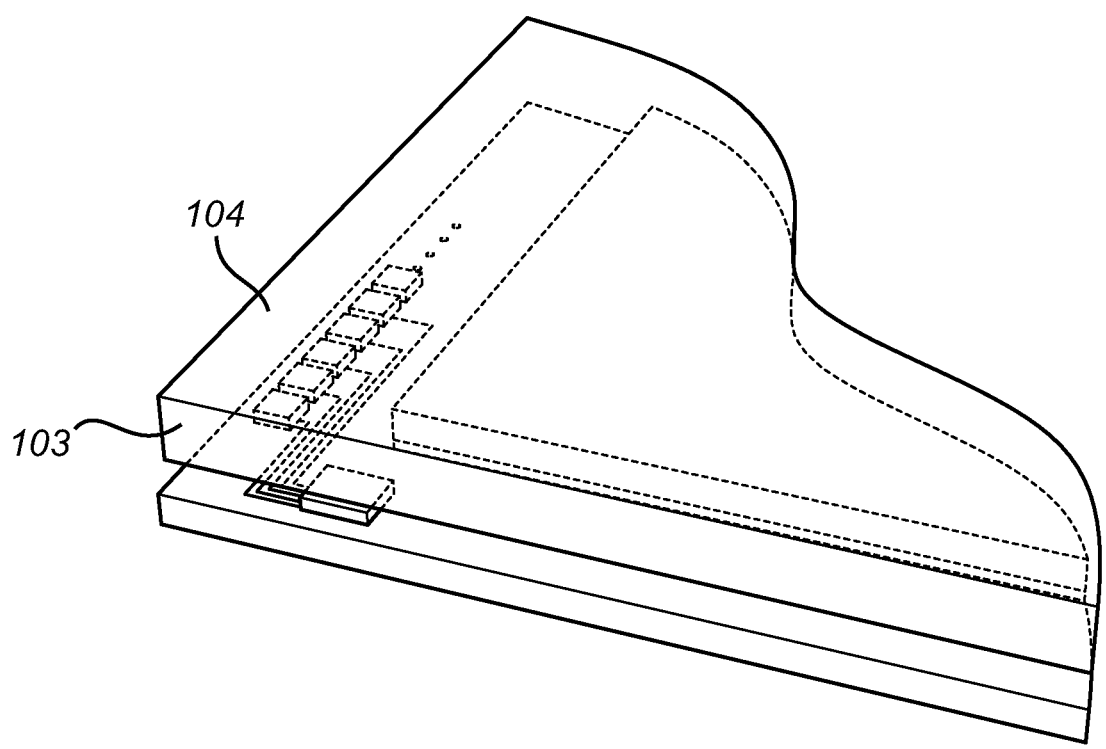

FIG. 7 is a flow chart outlining the general steps of manufacturing a display arrangement according to an embodiment of the invention. The method will be discussed with further reference to FIGS. 8A-D schematically illustrating steps of the manufacturing method.

The method comprises providing 700 a display panel 102 comprising a plurality of sub-layers 202, wherein one of the sub-layers 204 in the display panel 102 comprises a protruding portion 206 extending outside of an area of any other sub-layer. In the present description, the display panel 102 is an LCD-panel comprising a TFT-substrate layer 204, a TFT-layer 208 and a color filter layer 210. In practice, a display panel typically comprises a number of additional layers. However, all of the required layers are not illustrated herein to avoid cluttering the drawings. However, the described method is applicable also for different layer configurations and for different types of display panels.

Next, the electrically conductive lines 212 are formed 702 on the protruding portion 206 of the TFT-substrate layer 204. The electrically conductive lines 212 are arranged and configured to connect each ultrasonic transducer 106 to ultrasonic transducer control circuitry 114. The step of forming the connection lines 112 also comprises forming connection pads 800 for the transducers 106. The step of forming 702 electrically conductive lines 212 on the protruding portion may be performed either before or after the subsequent layers 208, 210 of the display panel are arranged on the layer 204 comprising the protruding portion 206. In the described example where the protruding portion 206 is formed in the TFT-substrate layer 204, it is advantageous to form the electrically conductive lines 212 for connecting the transducers in the same metal deposition and patterning steps where the thin-film-transistors of the TFT-layer 208 are formed.

If the protruding portion 206 is instead formed in a touch panel layer, the conductive lines may be formed in one of the conductive layers of the touch panel in a similar manner as described above.

Following formation of the conductive lines 112 and connection pads 800, a plurality of ultrasonic transducers 106 are arranged 704 on the protruding portion along the periphery of the display panel 102 and outside of an active display area of the display arrangement 200, such that the electrically conductive bottom electrode 110 of each transducer 106 is connected to a corresponding electrically conductive line 112 on the protruding portion 206 for connection to the control circuitry 114. In an example embodiment, the size of the transducer is approximately 500 μm×500 μm and the size of the connection lines 212 may vary.

It should however be noted that it may not be required to provide one connection line 112 for each transducer 106. Instead, routing and addressing solutions may be employed to provide a signal to the desired transducer 106 using a lower number of connection lines 112 similar to a data bus architecture.

In a final step, a cover plate 103 is arranged 706 on the display panel 102 such that the ultrasonic transducers 106 are located between the cover plate 103 and the protruding portion 206, the cover plate having a sensing surface 104 configured to be touched by a finger 105.

The method may also comprise arranging a supporting frame (not shown) around the display panel 102 or parts of the display panel 102 to facilitate assembly of an electronic device comprising the display arrangement.

Even though the invention has been described with reference to specific exemplifying embodiments thereof, many different alterations, modifications and the like will become apparent for those skilled in the art. Also, it should be noted that parts of the arrangement may be omitted, interchanged or arranged in various ways, the arrangement yet being able to perform the functionality of the present invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A display arrangement comprising an ultrasonic biometric sensing device for in-display biometric sensing, the display arrangement comprising:
   a cover plate having a sensing surface configured to be touched by a finger;
   a display panel comprising a plurality of sub-layers;
   a plurality of ultrasonic transducers arranged along the periphery of the display arrangement and outside of an active display area of the display arrangement, wherein the ultrasonic transducers are non-overlapping with an active sensing area of the biometric sensing device, each ultrasonic transducer comprising an electrically conductive top electrode located on a first side of the transducer facing the cover plate and an electrically conductive bottom electrode on a second side of the transducer, the second side opposing the first side; and
   ultrasonic transducer control circuitry connected to each of the ultrasonic transducers and configured to control the ultrasonic transducers to emit an ultrasonic signal propagating in the cover plate, to receive an ultrasonic signal having been influenced by an object in contact with the sensing surface and to determine properties of the object based on the received ultrasonic signal;
   wherein one of the sub-layers in the display panel comprises a protruding portion extending outside of an area of any other sub-layer located between the sub-layer comprising the protruding portion and the cover plate, and wherein the plurality of ultrasonic transducers are arranged on the protruding portion between the protruding portion and the cover plate such that a direct mechanical coupling between the transducer and the cover plate is formed.

2. The display arrangement according to claim 1, wherein the display panel comprises a thin film transistor-, TFT-layer and a TFT-substrate layer on which the TFT-layer is formed, and wherein the protruding portion is formed in the TFT-substrate layer.

3. The display arrangement according to claim 2, wherein at least one of the electrically conductive top electrode and the electrically conductive bottom electrode is routed and connected to the ultrasonic transducer control circuitry in a conductive layer located on the same substrate on which the TFT-layer is formed.

4. The display arrangement according to claim 1, wherein the display panel comprises a color filter layer, and wherein the protruding portion is formed in the color filter layer.

5. The display arrangement according to claim 1, wherein the display panel comprises an organic light emitting diode-, OLED-layer and an OLED-substrate layer on which the OLED-layer is formed, wherein the protruding portion is formed in the OLED-substrate layer.

6. The display arrangement according to claim 1, wherein the display panel comprises a liquid crystal display, LCD-layer and an LCD-substrate layer on which the LCD-layer is formed, wherein the protruding portion is formed in the LCD-substrate layer.

7. The display arrangement according to claim 1, wherein the display panel further comprises a capacitive touch sensitive panel, wherein the protruding portion is formed in a substrate layer of the touch sensitive panel.

8. The display arrangement according to claim 7, wherein at least one of the electrically conductive top electrode and the electrically conductive bottom electrode is routed and connected to the ultrasonic transducer control circuitry in a conductive layer comprised in the touch sensitive panel.

9. The display arrangement according to claim 8, wherein the ultrasonic transducer control circuitry is integrated in touch panel control circuitry of the display arrangement.

10. The display arrangement according to claim 1, wherein at least one of the electrically conductive top electrodes and the electrically conductive bottom electrode is routed and connected to the ultrasonic transducer control circuitry on the layer comprising the protruding portion.

11. The display arrangement according to claim 1, wherein the ultrasonic transducer control circuitry is integrated in display control circuitry of the display arrangement.

12. The display arrangement according to claim 1, wherein the electrically conductive top electrode and the electrically conductive bottom electrode is routed and connected to the ultrasonic transducer control circuitry via the cover plate.

13. The display arrangement according to claim 1, further comprising a connection material located between the transducer and the cover plate, mechanically coupling the transducer to the cover plate.

14. The display arrangement according to claim 1, wherein the electrically conductive bottom electrode comprises an electrically conductive spacer arranged between the bottom electrode and the protruding portion.

15. The display arrangement according to claim 1, wherein a transducer comprises one of the electrically conductive top or bottom electrode and a plurality of the other of the electrically conductive top or bottom electrodes such that an active portion of the transducer is defined by the plurality of electrically conductive top or bottom electrodes.

16. A method for manufacturing a display arrangement comprising an ultrasonic biometric sensing device for in-display biometric sensing, the method comprising:

providing a display panel comprising a plurality of sub-layers, wherein one of the sub-layers in the display panel comprises a protruding portion extending outside of an area of any other sub-layer located below the sub-layer comprising the protruding portion;

providing electrically conductive lines on the protruding portion, wherein the electrically conductive lines are configured to connect each ultrasonic transducer to ultrasonic transducer control circuitry configured to control the ultrasonic transducers to emit an ultrasonic signal propagating in a cover plate, to receive an ultrasonic signal having been influenced by an object in contact with a sensing surface of the cover plate and to determine properties of the object based on the received ultrasonic signal;

arranging a plurality of ultrasonic transducers on the protruding portion along the periphery of the display arrangement and outside of an active display area of the display arrangement, wherein the ultrasonic transducers are non-overlapping with an active sensing area of the biometric sensing device, each ultrasonic transducer comprising an electrically conductive top electrode located on a first side of the transducer and an electrically conductive bottom electrode on a second side of the transducer, the second side opposing the first side, wherein each electrically conductive bottom electrode is connected to a corresponding electrically conductive line on the protruding portion; and arranging a cover plate on the display panel such that the ultrasonic transducers are located between the cover plate and the protruding portion such that a direct mechanical coupling between the transducer and the cover plate is formed, the cover plate having a sensing surface configured to be touched by a finger.

17. The method according to claim 16, wherein the protruding portion is a TFT-substrate, and wherein forming the electrically conductive lines on the protruding portion comprises forming the electrically conductive lines in a conductive layer used in a TFT-manufacturing process.

18. The method according to claim 16, wherein the protruding portion is a touch sensitive panel, and wherein forming the electrically conductive lines on the protruding portion comprises forming the electrically conductive lines in a conductive layer used in a touch sensitive panel manufacturing process.

19. The method according to claim 16, further comprising arranging control circuitry on the protruding portion, and forming an electrical connection between each transducer and the control circuitry.

20. The method according to claim 16, further comprising arranging a rigid frame at least partially encircling the display panel, and forming a mechanical connection between the protruding portion and the frame.

\* \* \* \* \*